United States Patent
Alford et al.

(10) Patent No.: US 9,408,938 B1
(45) Date of Patent: Aug. 9, 2016

(54) ASPIRATING PHOTOCHEMICAL ODOR CONTROL SYSTEM FOR WASTEWATER LIFT STATION AND FORCE MAIN ODORS

(71) Applicants: Marvin F. Alford, Jacksonville, FL (US); Glenn Tyson, Jacksonville, FL (US)

(72) Inventors: Marvin F. Alford, Jacksonville, FL (US); Glenn Tyson, Jacksonville, FL (US)

(73) Assignee: ENERGY ENGINEERING SYSTEMS, LLC, Jacksonville, FL (US)

( * ) Notice: Subject to any disclaimer, the term of this patent is extended or adjusted under 35 U.S.C. 154(b) by 0 days.

(21) Appl. No.: 15/016,681

(22) Filed: Feb. 5, 2016

(51) Int. Cl.
*B01D 53/46* (2006.01)
*A61L 9/20* (2006.01)

(52) U.S. Cl.
CPC ....................................... *A61L 9/205* (2013.01)

(58) Field of Classification Search
CPC .......... A61L 9/205; A61L 9/20; B01D 53/46; C02F 2209/265; C02F 2209/235; C02F 2303/02
See application file for complete search history.

(56) References Cited

U.S. PATENT DOCUMENTS

| | | | |
|---|---|---|---|
| 8,337,759 B1 * | 12/2012 | Alford | C02F 1/78 422/120 |
| 2003/0075502 A1 * | 4/2003 | Mullerheim | B01D 61/16 210/615 |

* cited by examiner

*Primary Examiner* — Kishor Mayekar
(74) *Attorney, Agent, or Firm* — Mark Young, P.A.

(57) ABSTRACT

An aspirating photochemical odor control system allows odoriferous gases to reside in a wet well or force main (odor source) until gas pressure in the odor source forces the gases out. A check valve admits air into the odor source when pressure in the odor source decreases appreciably below ambient pressure. When pressure in the odor source exceeds ambient pressure, a check valve permits flow of gases from the odor source to a photochemical reaction chamber and solar thermal collector to react with oxidizer generated by UV lamps, before being exhausted to the atmosphere.

20 Claims, 5 Drawing Sheets

ASPIRATING PHOTOCHEMICAL ODOR CONTROL SYSTEM FOR WASTEWATER LIFT STATION AND FORCE MAIN ODORS

FIELD OF THE INVENTION

This invention relates generally to wastewater lift stations and force mains, and, more particularly, to an aspirating photochemical system for eliminating odors expelled from wastewater lift stations and force mains.

BACKGROUND

Wastewater lift Stations or Pump Stations are used to "lift" liquid uphill—against gravity. They are an essential component of a wastewater collection system which takes wastewater from residents and businesses in a community and pumps it to a sewage treatment plant.

Managing a network of wastewater lift stations that pumps to the treatment plant is challenging. Accidental discharge of sewerage is a serious environmental hazard. Pumps can block, level sensing devices can fail, pipes can crack, lightning or power surges can damage control equipment, and power to control pumps can be interrupted. Discharge of gases is also problematic. Not only are the discharged gases pollutants, but some are quite odoriferous. Thus, nearby residents and businesses may encounter extremely unpleasant odors originating from a nearby lift station. Foul odors escaping the wet well or force main air space has been a continual problem over the years, particularly in residential neighborhoods.

A force main is a pressurized main pipe that can carry water, sewage, and other materials to and from wastewater lift stations. Many force mains have a high point equipped with a relief valve to allow gas trapped between upstream and downstream liquid to vent to the atmosphere.

Odors are inevitable. Wastewater undergoing storage, transportation, and treatment will produce odors. The production of odors comes as a result of wastewater composition and depends on the environment and the time that the particular environmental conditions have existed. During some conditions, odors will escape through vents.

Gaseous emissions may include hydrogen sulfide ($H_2S$), ammonia ($NH_3$), carbon dioxide ($CO_2$), and methane ($CH_4$). Some other gases resulting from biological activity are nitrogen ($N_2$), oxygen ($O_2$), and hydrogen ($H_2$). Most common sewer gases are odorless except for hydrogen sulfide, which has the strong odor of rotten eggs, and ammonia, which has the odor of concentrated urine. The principal odor-causing gas in a wastewater lift station or force main is hydrogen sulfide.

Many methods have been used over the years to control or mask the foul odors including: 1) feed of chemicals such as hydrogen peroxide into the liquid; 2) aeration of the liquid; 3) chemical scrubbers; 4) biological scrubbers; 5) oxidation in the wet well or force main air space; and 6) activated carbon absorption. Chemicals can be extremely expensive. Several of the methods are not energy efficient or cost effective. Maintenance can also be expensive and cause excessive downtime of equipment. A cost effective odor reduction system that does not require replenishment of chemicals or a substantial capital investment is needed.

Further complicating matters, the volume and rate of odoriferous gases emitted can vary considerably based upon various factors, including temperature, dissolved oxygen, pH and well conditions such as volume. Hydrogen sulfide production increases at higher wastewater temperatures, and hydrogen sulfide released from wastewater will combine with water vapor to form sulfuric acid, which attacks sewers, manholes, wet well or force mains, and other facilities. The presence of certain types of gases in sewers depends on oxygen availability. When little oxygen is present, biological degradation is through anaerobic processes and the predominant gases released will be hydrogen sulfide and methane. Another condition that promotes the release of hydrogen sulfide gas is wastewater pH. Sulfide exists in wastewater in the ionic form above pH 7.5. Below pH 7.5, sulfide leaves the wastewater in the gaseous form. Yet another condition is the volume of wastewater in a well and vapor pressure. When the wastewater level falls due to pumps pumping the liquid from the wet well or force main, foul odor gases are not discharged and fresh air is sucked into the wet well or force main. However, when wastewater level rises due to increased wastewater production or precipitation, odoriferous gases are expelled. Thus, an effective odor reducing system must adapt to such changing conditions.

The system described in U.S. Pat. No. 8,337,759, while effective for reducing malodorous emissions, requires expensive equipment and frequent maintenance, and consumes considerable energy to power the oxygen concentrator and ozone generator.

Some other systems use pumps or fans to move odoriferous gases from the wet well or force main ullage through a deodorizing system. These systems operate even when pressure in the ullage of the wet well or force main does not exceed ambient pressure. Such systems expend considerable energy treating gases that would not otherwise escape the wet well or force main. They also expose expensive equipment with moving parts to corrosive and fouling gases and vapors.

Some other systems introduce oxidizers into the wet well or force main. Equipment (e.g., pumps), hardware and seals may undergo corrosion at an accelerated rate in the presence of the strong oxidizers.

Some other systems pass the odoriferous exhaust gases through chemical reactants (e.g., activated carbon). While effective for reducing odors, such reactants require periodic replacement. The replacement material and services can be costly.

What is needed is a system that allows odoriferous gases to reside in a wet well or force main until the pressure in the wet well or force main forces the gases out. The system should avoid locating any pumps or fans in the exhaust gas flow stream. The system should also allow the wet well or force main to draw in ambient air when the pressure in the wet well decreases appreciably below ambient pressure.

The invention is directed to overcoming one or more of the problems and solving one or more of the needs as set forth above.

SUMMARY OF THE INVENTION

A wet well and force main are referred to herein collectively as vented sewage transport facilities, with each being a vented sewage transport facility and an odor source. Odoriferous gases that accumulated in such facilities are vented to the atmosphere through one or more vents (e.g., exhaust ports, relief valves, etc. . . . ).

An aspirating photochemical odor control system according to principles of the invention allows odoriferous gases to reside in a wet well or force main until gas pressure in the wet well or force main forces the gases out. The system does not require any pumps, fans or sensors in the exhaust gas flow stream, any of which could be corroded and/or fouled by the gases. The wet well or force main is sealed, excepting one or more inlets and outlets for wastewater flow and a vent fluidly coupled to the flow path of the system. The system admits air into the wet well or force main when the pressure in the wet well or force main decreases appreciably below ambient pressure. Concomitantly, when the pressure in the wet well or force main decreases appreciably below ambient pressure, the system prevents backflow of strong oxidizers from a photochemical reaction chamber to the wet well or force main. Conversely, when the pressure in the wet well or force main increases appreciably above ambient pressure, the system permits flow of gases from the ullage of the wet well or force main to the photochemical reaction chamber, where the gases react with oxidizers generated in the reaction chamber.

To achieve these and other objectives, an exemplary aspirating photochemical odor control system according to principles of the invention includes an inlet tube having a first end and an opposite second end, the first end of the inlet tube is fluidly coupled to the odor source, such as a wet well or force main. A tube may be an integrally formed piece of tubing, or an assembly of several pieces of tubing. The tubing may be pipe of various shapes and sizes.

The exemplary system includes a photochemical reaction chamber that has an inlet port, an outlet port spaced apart from the inlet port, an exterior surface, an internal compartment, and a light source in the internal compartment. The second end of the inlet tube is fluidly coupled to the inlet port of the photochemical reaction chamber.

A first check valve in the inlet tube defines a flow path from an ambient atmosphere into the inlet tube. The first check valve prevents flow from the inlet tube to the ambient atmosphere. The first check valve opens and allows flow from the ambient atmosphere into the inlet tube when pressure in the inlet tube is less than a pressure of the ambient atmosphere (i.e., during negative pressure mode of operation).

A second check valve is provided in the inlet tube in fluid communication with the first end and second end of the inlet tube. The second check valve is disposed between the second end of the inlet tube and the first check valve. The second check valve prevents flow from the photochemical reaction chamber (i.e., backflow). The second check valve opens and allows flow from the first end of the inlet tube to the second end of the inlet tube when the pressure in the inlet tube exceeds the pressure of the ambient atmosphere.

The light source is a UV light source that produces ozone in the photochemical reaction chamber by photolysis of oxygen. The light source may be a plurality of UV lamps emitting UV light with wavelengths less (shorter) than 260 nanometers, e.g., at wavelengths of 175 to 195 nm, or at about 185 nm. The UV light source may be a low pressure mercury vapor lamp, medium pressure mercury vapor lamp, an LED lamp, or any combination of these, or any other lamps that emit light at the target wavelength.

A flue is provided as an exhaust flow path. The flue has an inlet and an outlet. The flue inlet is fluidly coupled to the outlet of the photochemical reaction chamber. The flue outlet is in fluid communication with the ambient environment, i.e., open to the atmosphere. Gases flowing from the system leave through the flue outlet.

The odor source may be a wet well or force main. An exemplary wet well or force main includes a container defining a sump for containing liquid and an ullage above the sump for containing gases, a liquid inlet port in the container, a liquid outlet port in the container, and a sealed vent port in the container. The first end of the inlet tube is fluidly coupled to the sealed vent port. The sealed vent port includes a port opening and a port cover. The port cover covers and hermetically seals the container. Gaskets and/or nonporous coverings may be used to preventing leaking from the wet well or force main through a port.

An exemplary force main is a pressurized main pipe that can carry water, sewage, and other materials to and from wastewater lift stations. Many force mains have a high point equipped with a relief valve to allow gas trapped between upstream and downstream liquid to vent to the atmosphere. The relief valve is sealed (e.g., sealed with a gasket) to prevent leakage, except through its outlet when the valve is open. The first end of the inlet tube is fluidly coupled to the outlet of the relief valve.

In an optional embodiment, the exterior surface of the photochemical reaction chamber may be substantially black so that the photochemical reaction chamber serves as a solar thermal collector. The temperature of the interior compartment increases due to solar thermal collection by the photochemical reaction chamber. Such increased temperature facilitates photochemical reaction in the photochemical reaction chamber.

A blower and a blower tube fluidly coupling the blower to the flue introduce air as a diluent into the flue to dilute the flue exhaust.

Optionally, an electric switch may be operably coupled to the second check valve and electrically coupled to a relay electrically coupled to the blower. The switch may cause the relay to activate the blower whenever the second check valve is open.

One or each check valve may be a flap valve having a flexible elastomeric flap and a corresponding annular valve seat in a valve tube. The flexible elastomeric flap abuts and covers the valve seat when in a closed configuration. The flexible elastomeric flap deflects away from the valve seat when in an open configuration.

In an optional configuration, the photochemical reaction chamber may be a serpentine arrangement of tubing having a plurality of fluidly coupled segments that cause a flow to proceed in opposite directions as the flow progresses from the inlet port to the outlet port.

BRIEF DESCRIPTION OF THE DRAWINGS

The foregoing and other aspects, objects, features and advantages of the invention will become better understood with reference to the following description, appended claims, and accompanying drawings, where:

Those skilled in the art will appreciate that the figures are not intended to be drawn to any particular scale; nor are the figures intended to illustrate every embodiment of the invention. The invention is not limited to the exemplary embodiments depicted in the figures or the particular components, shapes, configurations, relative sizes, ornamental aspects or proportions shown in the figures.

DETAILED DESCRIPTION

An aspirating photochemical odor control system according to principles of the invention allows odoriferous gases to reside in a sealed wet well or force main until gas pressure in the wet well or force main forces the gases out. A first check valve admits air into the wet well or force main when pressure in the wet well or force main decreases appreciably below ambient pressure. When pressure in the wet well or force main exceeds ambient pressure, a second check valve permits flow of gases from the wet well or force main to a photochemical reaction chamber and, optionally, solar thermal collector where the gases react with oxidizers generated by UV lamps in a heated environment before being exhausted to the atmosphere. The second check valve also prevents backflow from the reaction chamber into the wet well or force main. Exhausted gases flow through a flue open to the atmosphere. A blower may supply air to the flue to dilute exhausted gases.

Figure 1:
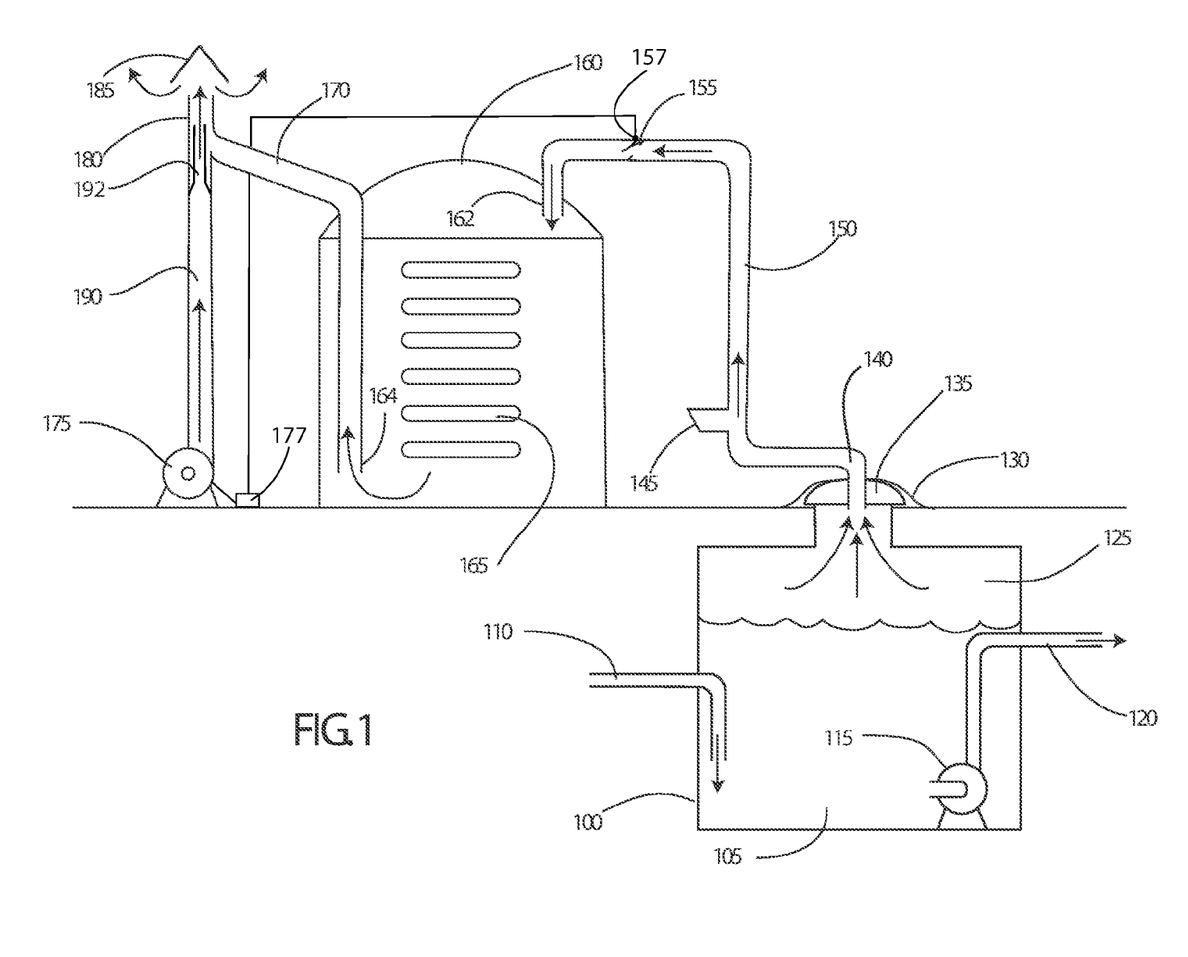
FIG. 1 is a high level schematic illustrating components of a system and steps of a photochemical odor control process, with a wet well expelling malodorous gases, according to principles of the invention.
Figure 2:
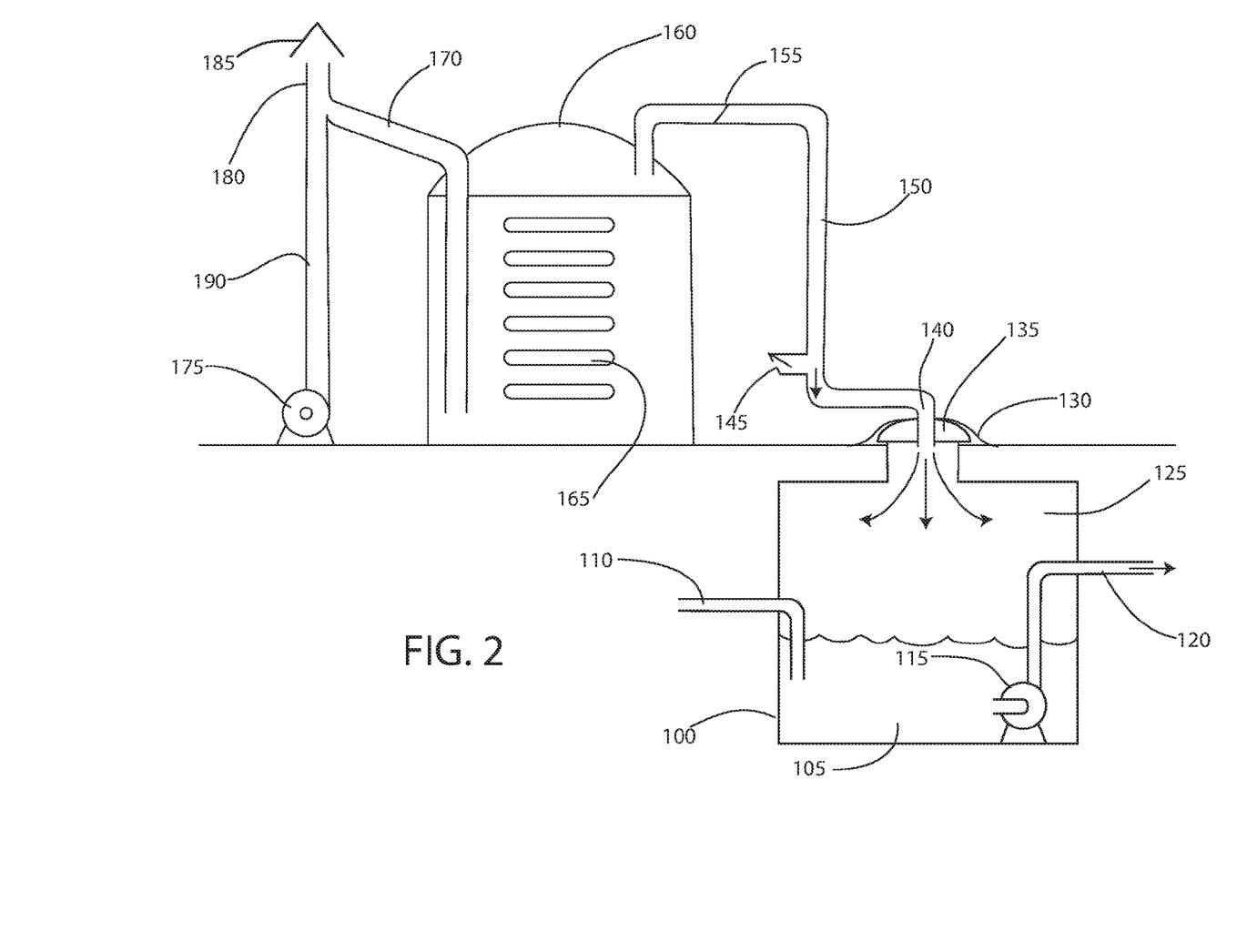
FIG. 2 is another high level schematic illustrating components of system and steps of a photochemical odor control process, with a wet well drawing in air, according to principles of the invention.

Referring to FIGS. 1 and 2, a wet well 100 is conceptually illustrated. The wet well or force main includes one or more wastewater inlets 110, a portion 105 containing wastewater, a space (i.e., ullage) 125 above the wastewater containing gases, a pump 115 and one or more wastewater outlets 120. As the wet well 100 receives wastewater through the inlet 110, the wastewater accumulates in the bottom portion 105 of the wet well or force main. The pump 115 urges accumulated wastewater from the bottom portion 105 through the outlet 120.

One or more access ports and vents may be provided at the top of the wet well 100. As the access ports tend to leak, even when closed with a cover, they provide means for odoriferous gases to escape from the wet well or force main, and a means for ground water to enter the wet well or force main. To avoid gas escape and water intrusion, the vent port is closed with a cover 135 and substantially sealed. Such sealing may be accomplished by installing a gasket beneath the cover (i.e., between the cover and port opening), by covering ports and vents using a substantially impermeable elastomeric material, and/or by installing nonporous caps over the ports and vents, including any covers. In FIGS. 1 and 2, an elastomeric seal 130 is shown covering the vent port cover 135. The elastomeric seal may comprise a sheet of plastic, synthetic rubber or natural rubber applied securely over the port. The seal 130 may be secured in place with a clamp. The seal 130 heremetically seals the vent port to the container of the wet well or force main. While the vent port cover 135 and seal 130 may be removable for maintenance and inspection, when they are attached they provide a hermetic seal.

The ullage of the wet well or force main is the space above the wastewater in the wet well or force main. Gases from the wastewater occupy the ullage.

An aspirating photochemical odor control system according to principles of the invention operates in two modes—a positive pressure mode and a negative pressure mode. In positive pressure mode the pressure of gases in the wet well or force main exceeds ambient pressure, while in negative pressure mode ambient pressure exceeds the pressure of gasses in the wet well or force main. Positive pressure mode typically occurs when pressure in the ullage of the wet well or force main increases due to rising wastewater level, expansion of gases due to rising temperature, or any other condition that increases formation of gases from wastewater in the wet well or force main. As one nonlimiting example, a decrease in dissolved oxygen in the wastewater promotes release of hydrogen sulfide gas.

Negative pressure mode typically occurs when the wastewater level in the wet well or force main drops, such as due to a low flow rate of wastewater into the wet well or force main. When the volumetric flow rate of wastewater leaving the wet well or force main exceeds the volumetric flow rate of wastewater entering the wet well or force main, the wastewater level in the wet well or force main decreases. As a wet well or force main according to principles of the invention is substantially sealed, except for the wastewater inlet and outlet, a decrease in wastewater level causes an increase in ullage volume and an attendant decrease in pressure of gases in the ullage.

As the wet well or force main is substantially sealed, the changing level of wastewater in the wet well or force main act like a piston. Gases above the wastewater are exhausted from the wet well or force main as the wastewater level rises and increases the pressure of gases in the ullage to a pressure in excess of ambient pressure. Gases above the wastewater are not exhausted from the wet well or force main as the wastewater level drops and decreases the pressure of gases in the ullage to a pressure below ambient pressure.

A vent tube 140 extends through the covered port 135 of the wet well 100. In positive pressure mode, gases may flow from the ullage 125 of the wet well 100 into the vent tube 140. In negative pressure mode, gases (e.g., air) may flow from the ambient environment through the vent tube 140 into the ullage 125.

A check valve 145 (i.e., one-way valve) allows gases (e.g., air) to flow from the ambient environment through the vent pipe 140 into the ullage 125 during negative pressure mode operation. The check valve 140 prevents gases from the ullage 125 from flowing through through the check valve 140 during positive pressure mode operation. The check valve may comprise a tilted flap valve, having a flap that is deflectable to allow flow in one direction through the valve.

The check valve 145 is in fluid communication with a transitional tube 150, which leads from the vent tube 140 to a photochemical reaction chamber 160. The transitional tube 150 may be fluidly coupled to the vent tube 140 or integrally formed with the vent tube.

Another check valve 155 may be located in the transitional tube 150 near the entrance to the photochemical reaction chamber 160. This check valve 155 allows gases to flow into the photochemical reaction chamber, when the system is operating in positive pressure mode. When the system operates in negative pressure mode, the transitional check valve 155 disposed in the flow path between the photochemical reaction chamber 160 and wet well 100 prevents the flow of gases from the photochemical reaction chamber 160 to the well well 100. The photochemical reaction chamber 160 generates strong oxidizers, including ozone, which can damage pumps, seals, and metallic, rubber and plastic components in the wet well 100, especially over time. Additionally, reactions between such oxidizers and odoriferous gases in the wet well or force main may lead to formation of acids, including highly corrosive sulfuric acid. To avoid damage from backflow, the check valve 155 (a backflow preventer) prevents flow from the photochemical reaction chamber 160 into the wet well 100 (i.e., backflow) when the system is in negative pressure mode. While such backflow prevention allows odoriferous gases to reside and accumulate in the ullage of the wet well or force main without an induced reaction with an oxidizer, such residence and accumulation is not of concern. The sealed wet well 100 will retain all (or substantially all) of the odoriferous gases during operation in negative pressure mode. Thus, a system according to principles of the invention avoids introduction of potentially damaging gases into the wet well or force main during operation in negative pressure mode.

Optionally, an electrical switch or sensor may be coupled to either or both of the check valves 145, 155. Such a switch may be triggered when the check valve opens and closes. Such a switch may control a circuit with a relay that activates and deactivates another component such as the blower 175. By way of example, the switch 157 may close (i.e., complete a circuit) when check valve 155 opens. The check valve 155 opens when the system operates in positive pressure mode. The switch 157 may be coupled to a relay 177 that activates the blower 175. When the check valve 155 opens, the switch 157 closes and completes a circuit that energizes the relay 177 that activates the blower 175. When the check valve 155 closes, the switch 157 opens and breaks the circuit to the relay 177, thereby deactivating the blower 175. In this manner, the blower 175 operates only when the system operates in positive pressure mode.

The photochemical reaction chamber 160 is a substantially sealed container, except for one or more inlets 162 and one or more outlets 164. Preferably, the inlet 162 and outlet 164 are spaced about as far apart as the chamber 160 allows. At a minimum, the inlet 162 and outlet 164 should be spaced a substantial distance apart (e.g., at least half the height of the chamber, and at least half the width or diameter of the chamber). This spacing maximizes the reaction time for gases in the chamber 160.

The chamber 160 is preferably comprised of corrosion resistant materials. Plastics that can withstand prolonged exposure to oxidizers and corrosive acid are preferred. Non-limiting examples include fluoroplastics (e.g., PTFE), polyphenylene oxides, polybutylene terephthalate (PBT), polyethylene terephthalate (PET), and polyvinyl chloride (PVC). The particular choice of material will depend upon the concentration and strength of the potentially harmful reactants.

In an exemplary embodiment, the chamber 160 is black and exposed to sunlight. As a black body, the chamber 160 absorbs most incoming sunlight. The absorbed light (electromagnetic radiation) interacts with the atoms and molecules of the chamber 160, causing the energy of the absorbed light to be converted into other forms of energy, such as heat. Thus, the chamber may optionally also be a solar thermal collector, absorbing light and generating heat. Concomitantly, the UV lamps generate heat. The combined generated heat facilitates desired photochemical reactions within the chamber. An internal temperature that reaches in excess of 100° F. is preferred and in excess of 125° F. is particularly preferred. Such temperatures are attainable in many geographical locations, for at least most of the year.

The chamber size may vary according to the size and output of the wet well or force main being treated. A chamber providing 50 gallons of storage volume or more will suffice for many wet well or force mains. However, the invention is not limited to any such particular size or shape of chamber. In an alternative embodiment, the reaction chamber may comprise a reticulate serpentine arrangement of tubing through which the gases flow. An example of such an alternative reaction chamber is discussed more fully below with reference to FIG. 4.

While one reaction chamber 160 is shown in FIGS. 1 and 2, the invention is not limited to use of one chamber 160. Rather, more than one reaction chamber may be used. A plurality of reaction chambers may be arranged in series and/or in parallel, in accordance with the principles of the invention.

The chamber 160 may optionally contain baffles (i.e., flow-directing or obstructing vanes, panels, or other structures) to enhance efficiency by maximizing residence time for reactions to occur within the chamber 160. However, the invention is not limited to a chamber 160 containing baffles.

An ultraviolet (UV) light source 165 contained within the reaction chamber 160 irradiates the gases exhausted from the wet well 100. The irradiation causes photochemical reactions convert odoriferous gases into compounds of little or no concern from an odor-causing and environmental standpoint. The UV light source may be a low pressure mercury vapor lamp, medium pressure mercury vapor lamp, an LED lamp, or any combination of these, or any other lamps that emit light at the target wavelength.

Referring again to FIGS. 1 and 2, differences between positive and negative pressure modes are illustrated. In positive pressure mode, gases are urged from the ullage 125 of the wet well 100, check valve 145 is closed, and check valve 155 is opened. Thus, gases flow from the wet well 100 into the reaction chamber 160 during positive pressure mode of operation, as illustrated in FIG. 1.

In contrast, during negative pressure mode of operation, check valve 145 may be opened to admit ambient air, depending upon the negative pressure. If the pressure differential between ambient pressure and the negative pressure of the wet well or force main is sufficient to open the valve 145, the valve will then open. Otherwise, it will remain closed. Check valve 155 will remain closed during operation in negative pressure mode. Thus, oxidizing gases accumulating in the reaction chamber 160 will not be drawn into the wet well 100.

Figure 3:
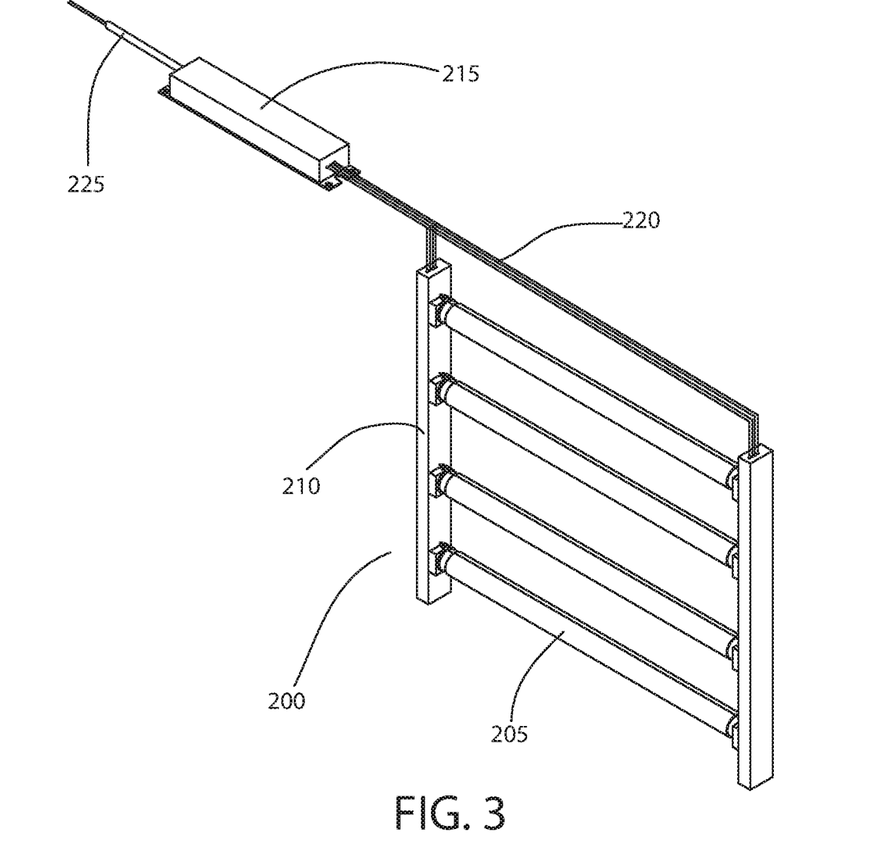
FIG. 3 is a schematic of an exemplary UV light assembly for a photochemical reaction chamber for a photochemical odor control system and process according to principles of the invention.

With reference to FIG. 3, in an exemplary embodiment, the UV light source 200 may comprise a plurality of fluorescent UV lamps 205, each of which may be energized through a ballast 215 and contained in a fixture 210. The ballast 215 includes leads 220 for the lamps 205, and a power supply lead 225 for power supplied from a utility power source, inverter, battery bank or other suitable power supply. The ballast 215 regulates current supplied to the lamps 205. In a particular preferred embodiment, four 10 to 40 watt UV lamps (e.g., four 30 watt lamps) are provided. However, the number, arrangement, mounting and power rating of the lamps may vary considerably without departing from the scope of the invention. The UV light source may be comprised of one or more low pressure mercury vapor lamps, medium pressure mercury vapor lamp, an LED lamp, or any combination of these, or any other lamps that emit light at the target wavelength.

In a preferred embodiment, the lamps emit short wave, germicidal, UVC radiation. In a particular preferred embodiment, the lamps emit radiation at a wavelength of 100 to 290 nm. In a more particular preferred embodiment, the lamps emit high energy ultraviolet photons (i.e., packets of light energy with wavelengths less (shorter) than 260 nanometers). In an exemplary embodiment lamps emitting radiation at a wavelength of about 185 nm±10% (e.g., 175 to 195 nm, preferably 185 nm) are used. The use of such short wave UV radiation has been found to be particularly effective for efficiently producing ozone and other oxidizers due to photoionization and substantially reducing odoriferous gas emissions.

Photolysis of $O_2$ in the exhaust gases by the UV lamps 205 produces monatomic oxygen, as shown below, where h is Planck's constant, v is frequency of the light, λ is the wavelength of the light, and c is the speed of light.

$$O_2 + hv \rightarrow O + O$$

where: $v = c/\lambda$

Monatomic oxygen O reacts with diatomic oxygen $O_2$ to produce ozone $O_3$.

$$O + O_2 \rightarrow O_3$$

Hydrogen sulfide ($H_2S$) reacts with ozone ($O_3$) to produce sulfur dioxide ($SO_2$) and water ($H_2O$).

$$H_2S + O_3 \rightarrow SO_2 + H_2$$

The UV radiation may also provide the energy necessary to spark the decomposition of ozone ($O_3$) to monatomic oxygen (O), which, in the presence of water vapor ($H_2O$), may lead to the formation highly reactive oxidizing hydroxyl radicals (.OH) by H abstraction from $H_2O$.

$$O + H_2O \rightarrow .OH + .OH$$

Regardless of the particular exhaust gases from the wet well or force main and the particular chemical reactions proceeding in the chamber 160, the effect of irradiating the exhaust gases from a wet well or force main with short wave, germicidal, UVC radiation, in the manner described above, to cause photolysis, appreciably reduces odoriferous gases in the exhaust stream.

The products of photolysis and the oxidation reactions, flow through the outlet tube 164 to an exhaust tube 170 to a flue 180. The exhaust is emitted from the flue 180 to the atmosphere. A cap 185 may optionally be provided over the flue 180 to prevent rain water from entering the flue 180.

Optionally, a blower 175 or fan blows ambient air through a blower outlet to the flue 180. The blower outlet may comprise a small diameter tube (e.g., 2-inch diameter) 192 within a concentric larger diameter tube 190 (e.g., 2-inch diameter). The end of the smaller diameter tube 192 terminates a distance (e.g., 2 to 12, preferably about 8 inches) from the end of the flue 180. The smaller diameter tube 192 provides a constriction that decreases pressure. The ambient air acts as a diluent, meaning it dilutes any odoriferous gases that may remain in the exhaust stream. Via a venturi effect, the ambient air stream drawing exhaust from the exhaust tube 170 and out of the flue 180. Use of such a blower 175 is optional. As the blower 175 is not in the flow path of the exhaust gases, it avoids corrosion and fouling from the exhaust gases. In an embodiment without a blower 175, the blower outlet tubes 190, 192 may be eliminated, and flow may proceed from exhaust tube 170 to the flue 180, without intersecting blower outlet tubes 190, 192. As used herein, the term blower encompasses any and all types of centrifugal fans.

The shapes, dimensions and routing of pipes or tubing may vary considerably without departing from the scope of the invention. Additional check valves may be included within the scope of the invention. Additional reaction chambers, whether in series or parallel, and additional UV lights may be provided, without departing from the scope of the invention. The flue 180 may be raised or lowered and configured to direct exhaust gases in a direction other than upwardly, without departing from the scope of the invention. These and other modifications will be apparent to those of ordinary skill in the art to which the invention pertains.

Figure 4:
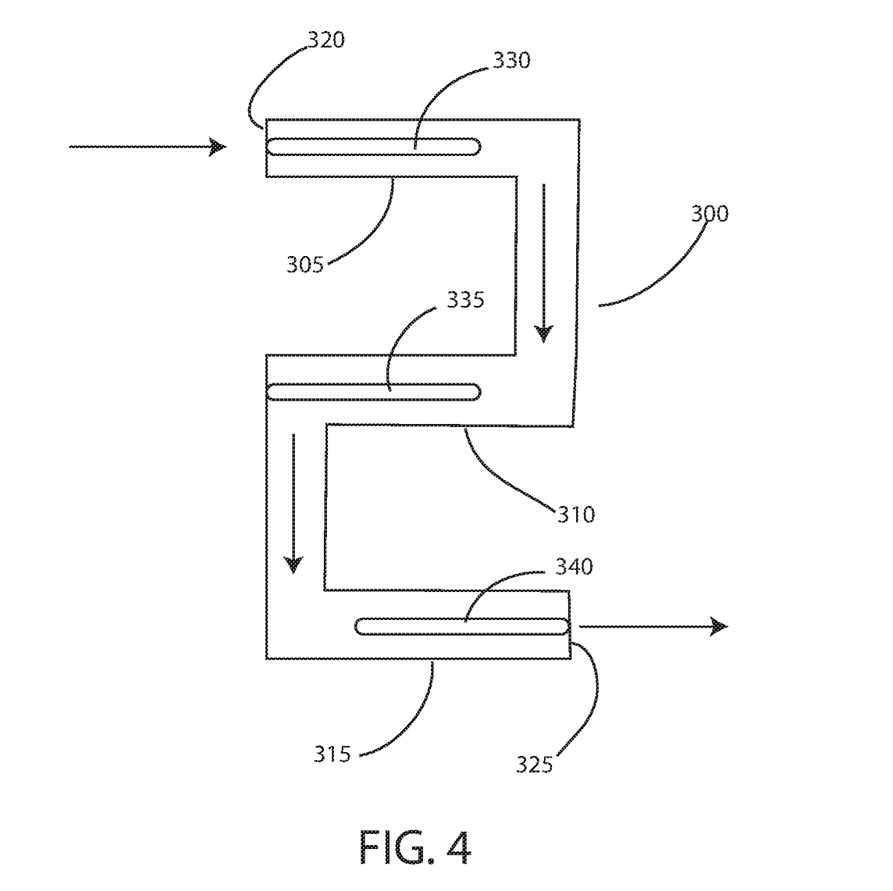
FIG. 4 is a schematic of an optional exemplary reticulated serpentine reaction chamber containing a plurality of UV lights in series in the flow path according to principles of the invention.

Referring to FIG. 4, a schematic of an optional exemplary reticulated serpentine reaction chamber 300 containing a plurality of UV lights 330, 335, 340 in series, each in a separate segment 305, 310, 315 of the serpentine flow path, from an inlet 320, to an outlet 325, is conceptually illustrated. The plurality of fluidly coupled segments 305, 310, 315 cause a flow to proceed in opposite directions as the flow progresses from the inlet 320 to the outlet 325. Such a configuration helps to maximize photolysis by increasing exposure time of gases to the light source and proximity to the light source. The invention is not limited to such a chamber 300 with three segments 305, 310, 315 as shown. Rather, serpentine chambers 300 with more than three segments may be utilized. Additionally, more than one serpentine chamber 300 may be utilized in series and/or in parallel.

Figure 5:
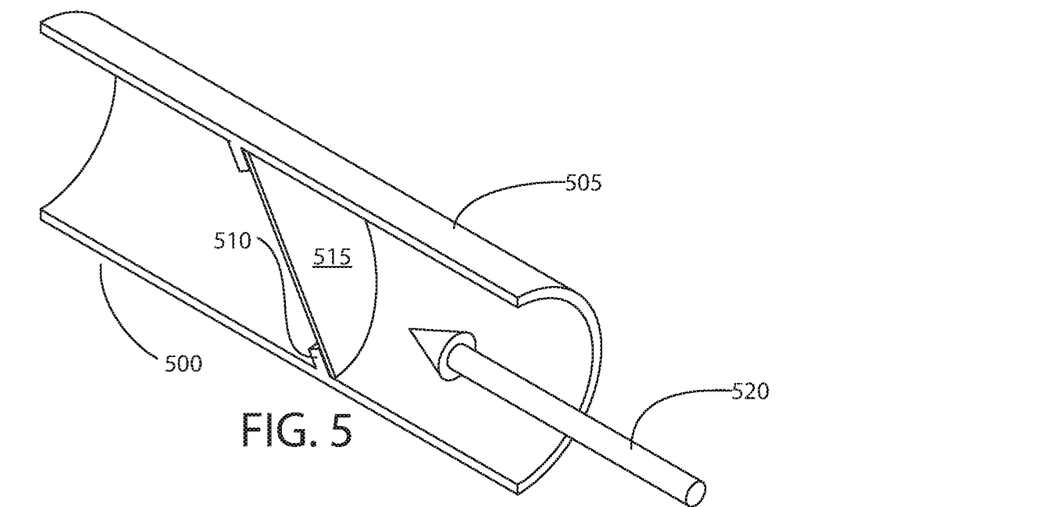
FIG. 5 is a perspective section view of an exemplary check valve in a closed position according to principles of the invention.
Figure 6:
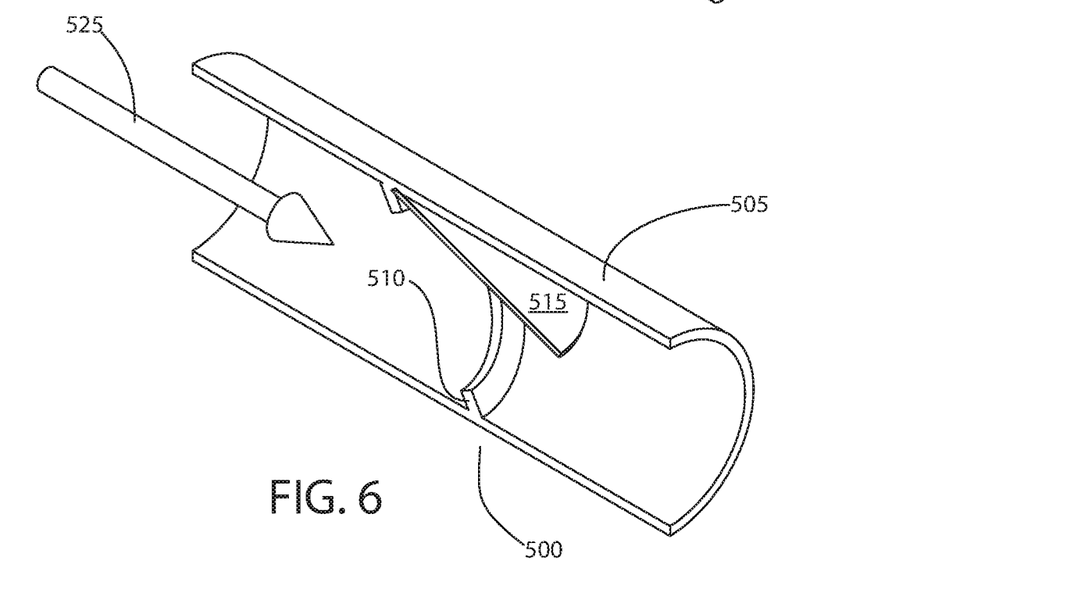
FIG. 6 is a perspective section view of an exemplary check valve in an opened position according to principles of the invention.

Referring now to FIGS. 5 and 6, perspective section views of an exemplary check valve in a closed position and in an open position according to principles of the invention, are provided. The valve includes a flexible flap 515 seated against an annular valve seat 510 within the interior of a housing such as a pipe 505. If the flow path is horizontal or substantially horizontal, the valve seat 510 is angled to facilitate closure of the flap 515. Such angling entails positioning the bottom of the valve seat 510 upstream from the top of the valve seat 510 relative to the flow to be blocked by the valve 500. If the flow path is vertical or substantially vertical, the flap and seat may be arranged horizontally, with the flap resting against the top side of the seat when closed. With either orientation, the flow to be blocked 520 urges the flap 515 against the valve seat 510. The flow to be allowed 525, urges the flap 515 away from the valve seat 510. Thus, a check valve according to principles of the invention allows flow in one direction, but not in the opposite direction.

The flap 515 may be made of a durable resilient elastomeric material that withstands the conditions of the flow path. Non-limiting examples include natural rubber, synthetic rubber, polymers of the organic compound isoprene, artificial elastomer synthesized from petroleum byproducts, and/or any of various plastics with sufficient resiliency to deflect to an opened position under the influence of a positive relative pressure in the direction of the allowed flow. When such pressure ceases, the resilient flap returns to the seated closed position.

In sum, an aspirating photochemical odor control system according to principles of the invention allows odoriferous gases to reside in a wet well or force main until gas pressure in the wet well or force main forces the gases out. The system does not require any pumps, fans or sensors in the exhaust gas flow stream, any of which could be corroded and/or fouled by the gases. The wet well or force main is sealed, excepting one or more inlets and outlets for wastewater flow and a vent fluidly coupled to the flow path of the system. The system allows the wet well or force main to draw in ambient air when the pressure in the wet well or force main decreases appreciably below ambient pressure. Concomitantly, when the pressure in the wet well or force main decreases appreciably below ambient pressure, the system prevents backflow of strong oxidizers from the photochemical reaction chamber to the wet well or force main. Conversely, when the pressure in the wet well or force main increases appreciably above ambient pressure, the system permits flow of gases from the ullage of the wet well or force main to the photochemical reaction chamber, where the gases react with oxidizers generated in the reaction chamber.

A system according to principles of the invention aspirates, meaning it draws in air in negative pressure mode and exhausts gases in positive pressure mode. The system does not require compressors, pumps, fans or blowers to blow, suck or otherwise propel gases from the wet well or force main to the reaction chamber. The system does not continuously remove gases from the wet well or force main. Instead, odoriferous gases are allowed to remain within the confines of the wet well or force main in negative pressure mode, which may comprise a significant portion of each day. The system admits odoriferous gases from the wet well or force main into the reaction chamber only in positive pressure mode and only under the influence of the pressure generated by the wet well or force main.

While an exemplary embodiment of the invention has been described, it should be apparent that modifications and variations thereto are possible, all of which fall within the true spirit and scope of the invention. With respect to the above description then, it is to be realized that the optimum relationships for the components and steps of the invention, including variations in order, form, content, function and manner of operation, are deemed readily apparent and obvious to one skilled in the art, and all equivalent relationships to those illustrated in the drawings and described in the specification are intended to be encompassed by the present invention. The above description and drawings are illustrative of modifications that can be made without departing from the present invention, the scope of which is to be limited only by the following claims. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents are intended to fall within the scope of the invention as claimed.

What is claimed is:

1. An aspirating photochemical odor control system for an odor source, the aspirating photochemical odor control system comprising:
   an inlet tube having a first end and an opposite second end, the first end of the inlet tube being fluidly coupled to the odor source;
   a photochemical reaction chamber having an inlet port, an outlet port, an exterior surface, an internal compartment, and a light source in the internal compartment;
   the second end of the inlet tube being fluidly coupled to the inlet port of the photochemical reaction chamber;
   a first check valve in the inlet tube defining a flow path from an ambient atmosphere into the inlet tube, said first check valve preventing flow from the inlet tube to the ambient atmosphere, and said first check valve opening and allowing flow from the ambient atmosphere into the inlet tube when a pressure in the inlet tube is less than a pressure of the ambient atmosphere;
   a second check valve in the inlet tube in fluid communication with the first end and second end of the inlet tube, the second check valve being disposed between the second end of the inlet tube and the first check valve, the second check valve preventing flow from the photochemical reaction chamber, and the second check valve opening and allowing flow from the first end of the inlet tube to the second end of the inlet tube when the pressure in the inlet tube exceeds the pressure of the ambient atmosphere;
   the light source being a UV light source configured to produce ozone in the photochemical reaction chamber by photolysis of oxygen; and
   a flue having a flue inlet and a flue outlet, the flue inlet being fluidly coupled to the outlet of the photochemical reaction chamber, and the flue outlet being in fluid communication with the ambient environment.

2. The aspirating photochemical odor control system according to claim 1, the odor source comprising a force main, the force main comprising a pipe with a gas relief valve, the gas relief valve having an outlet through which gases under pressure in the pipe are vented.

3. The aspirating photochemical odor control system according to claim 1, the odor source comprising a wet well, the wet well including a container defining a sump for containing liquid and an ullage above the sump for containing gases, a liquid inlet port in the container, a liquid outlet port in the container, and a sealed vent port in the container, the first end of the inlet tube being fluidly coupled to the sealed vent port, the sealed vent port including a port opening and a port cover, the port cover covering and hermetically sealing the container.

4. The aspirating photochemical odor control system according to claim 3, the light source comprising a plurality of UV lamps emitting UV light with wavelengths shorter than 260 nanometers.

5. The aspirating photochemical odor control system according to claim 4, the plurality of UV lamps emitting UV light at wavelengths of 175 to 195 nm.

6. The aspirating photochemical odor control system according to claim 4, the plurality of UV lamps emitting UV light at a wavelength of about 185 nm.

7. The aspirating photochemical odor control system according to claim 3, the exterior surface of the photochemical reaction chamber being substantially black and the photochemical reaction chamber comprising a solar thermal collector, a temperature of the internal compartment increased due to solar thermal collection by the photochemical reaction chamber, the increased temperature facilitating photochemical reaction in the photochemical reaction chamber.

8. The aspirating photochemical odor control system according to claim 3, the internal compartment of the photochemical reaction chamber having a height and a width, the second end of the inlet tube and the flue inlet being spaced apart by at least half the height of the internal compartment and at least half the width of the internal compartment.

9. The aspirating photochemical odor control system according to claim 3, the internal compartment of the photochemical reaction chamber containing at least one baffle disposed in the internal compartment between the second end of the inlet tube and the flue inlet.

10. The aspirating photochemical odor control system according to claim 3, further comprising a blower and a blower tube, the blower tube fluidly coupling the blower to the flue, and the blower blowing ambient air as a diluent through the blower tube, through the flue and out through the flue outlet.

11. The aspirating photochemical odor control system according to claim 10, further comprising an electric switch operably coupled to the second check valve, a relay electrically coupled to the blower, the switch being electrically coupled to the relay and causing the blower to operate when the second check valve is open.

12. The aspirating photochemical odor control system according to claim 3, the first check valve comprising a flap valve having a flexible elastomeric flap and a corresponding annular valve seat in a valve tube, the flexible elastomeric flap abutting and covering the valve seat when in a closed configuration and the flexible elastomeric flap deflecting away from the valve seat when in an open configuration, said valve seat being disposed within the valve tube between the flexible elastomeric flap and the ambient atmosphere.

13. The aspirating photochemical odor control system according to claim 3, the second check valve comprising a flap valve having a flexible elastomeric flap and a corresponding annular valve seat in a valve tube, the flexible elastomeric flap abutting and covering the valve seat when in a closed configuration and the flexible elastomeric flap deflecting away from the valve seat when in an open configuration, said flexible elastomeric flap being disposed within the valve tube between the valve seat and the second end of the inlet tube.

14. The aspirating photochemical odor control system according to claim 3, the photochemical reaction chamber comprising a serpentine arrangement of tubing having a plurality of fluidly coupled segments that cause a flow to proceed in opposite directions as the flow progresses from the inlet port to the outlet port.

15. The aspirating photochemical odor control system according to claim 3, the port cover including an outer cover and a port gasket, the gasket being disposed between the port opening and the outer cover, and the port cover being attached to and covering the port opening.

16. The aspirating photochemical odor control system according to claim 3, the port cover comprising a nonporous covering.

17. An aspirating photochemical odor control system for a sewage transport facility, the aspirating photochemical odor control system comprising:
   a sewage transport facility including a container defining a sump for containing liquid and an ullage above the sump for containing gases, a liquid inlet port in the container, a liquid outlet port in the container, a vent port in the container, and a port cover covering and sealing the vent port, the first end of the inlet tube being fluidly coupled to the vent port;
   an inlet tube having a first end and an opposite second end, the first end of the inlet tube being fluidly coupled to the vent port of the sewage transport facility;
   a photochemical reaction chamber having an inlet port, an outlet port spaced apart from the inlet port, an exterior surface, an internal compartment, and a light source in the internal compartment;
   the second end of the inlet tube being fluidly coupled to the inlet port of the photochemical reaction chamber;
   a first check valve in the inlet tube defining a flow path from an ambient atmosphere into the inlet tube, said first check valve preventing flow from the inlet tube to the ambient atmosphere, and said first check valve opening and allowing flow from the ambient atmosphere into the inlet tube when a pressure in the inlet tube is less than a pressure of the ambient atmosphere;
   a second check valve in the inlet tube in fluid communication with the first end and second end of the inlet tube, the second check valve being disposed between the second end of the inlet tube and the first check valve, the second check valve preventing flow from the photochemical reaction chamber, and the second check valve opening and allowing flow from the first end of the inlet tube to the second end of the inlet tube when the pressure in the inlet tube exceeds the pressure of the ambient atmosphere;
   the light source being a UV light source configured to produce ozone in the photochemical reaction chamber by photolysis of oxygen, the light source comprising a plurality of UV lamps emitting UV light with wavelengths shorter than 260 nanometers; and
   a flue having a flue inlet and a flue outlet, the flue inlet being fluidly coupled to the outlet of the photochemical reaction chamber, and the flue outlet being in fluid communication with the ambient environment.

18. The aspirating photochemical odor control system according to claim 17, the plurality of UV lamps emitting UV light at a wavelength of about 185 nm.

19. The aspirating photochemical odor control system according to claim 17, the exterior surface of the photochemical reaction chamber being substantially black and the photochemical reaction chamber comprising a solar thermal collector, a temperature of the internal compartment increased due to solar thermal collection by the photochemical reaction chamber, the increased temperature facilitating photochemical reaction in the photochemical reaction chamber.

20. The aspirating photochemical odor control system according to claim 17, further comprising a blower and a blower tube, the blower tube fluidly coupling the blower to the flue, and the blower blowing ambient air as a diluent through the blower tube, through the flue and out through the flue outlet.

* * * * *